United States Patent

Branemark

Patent Number: 5,362,236
Date of Patent: Nov. 8, 1994

[54] METHOD FOR ATTACHING A DENTAL FIXTURE IN BONE TISSUE

[75] Inventor: Per-Ingvar Bränemark, Mölndal, Sweden

[73] Assignee: Medevelop AB, Sweden

[21] Appl. No.: 154,183

[22] Filed: Nov. 18, 1993

[30] Foreign Application Priority Data

Nov. 26, 1992 [SE] Sweden .............. 9203563-3

[51] Int. Cl.$^5$ .............................................. A61C 8/00
[52] U.S. Cl. ..................................... 433/173; 433/174
[58] Field of Search ............... 433/173, 174, 175, 176, 433/201.1

[56] References Cited

U.S. PATENT DOCUMENTS

| | | | |
|---|---|---|---|
| 3,499,222 | 3/1970 | Linkow et al. | 433/174 |
| 5,052,930 | 10/1991 | Lodde et al. | 433/173 |
| 5,104,318 | 4/1992 | Piche et al. | 433/174 |
| 5,199,873 | 4/1993 | Schulte et al. | 433/173 |

FOREIGN PATENT DOCUMENTS

0438048  1/1991  European Pat. Off. .......... 433/174

*Primary Examiner*—John J. Wilson
*Attorney, Agent, or Firm*—Ostrolenk, Faber, Gerb & Soffen

[57] ABSTRACT

A substantially cylindrical anchoring element for implantation in bone tissue is constructed to support prostheses, such as artificial joint components, tooth bridges or artificial teeth etc. The anchoring element has two cylindrical segments with end portions differing in diameter. The end portion with the smaller diameter is positioned at the distal or insertion part of the element and at least parts of both end portions are provided with a threaded portion having the same pitch. The anchoring element is implanted by forming relatively large and relatively small diameter aligned passages in the bone tissue. The smaller diameter segment of the anchoring element passes through the relatively large diameter passage and is self threaded in the small diameter passage. While self threading by the smaller diameter segment takes place, the larger diameter segment is self threaded in the large diameter passage. The proximal end of the anchoring element is provided with a bore having internal threads formed about an axis that is tilted with respect to a common axis for the cylindrical segments. External threads on a prosthesis threadably engage the internal threads to secure such prosthesis to the anchoring element.

4 Claims, 2 Drawing Sheets

METHOD FOR ATTACHING A DENTAL FIXTURE IN BONE TISSUE

The present invention relates to an implant anchoring element, preferably for bone tissue integration, consisting of a mainly rotation-symmetric body made of a biocompatible material and of which one end is designed for supporting of prosthetic appliances, artificial joint components, dental bridge constructions, artificial teeth etc. and which on its outer surface is provided with an external screw thread, as well as a method to apply such an anchoring element in the maxilla and the zygomatic bone for retention of a tooth prosthesis or a bridge construction.

The invention can be advantageously used for any application where a double anchoring of such prosthetic appliances are desirable with regard to possible defects in the bone tissue, long bones etc., or in cases where a double retention is necessary for additional position fixation of the anchorage, e.g. by the reconstruction of finger joints, wrist joints etc.

In the following the invention will be described for its application as a fixture for the retention of artificial teeth or bridge constructions, without limiting its utilization for this type of use.

BACKGROUND

In general, partially or completely edentolous upper jaws can be treated by drilling holes in the jawbone and the consequent insertion of anchoring elements in these holes by the use of preferably cylindrical fixtures with an outer thread and to supply them with single-tooth or bridge prostheses in the latter case with more than one fixture to be applied in the bone in order to retain a bridge construction.

In certain cases when the patient has been edentolous for a long time and for this reason the jawbone has been partly resorbed, the dimension and the retention force of the jawbone is inadequate for the anchoring of one or several fixtures. The patient may thus not be successfully treated with a desirable prosthetic appliance, or may not be willing to accept the risk which in such a case may be considerable, for loosing the prosthesis or a fractured jawbone.

SUMMARY OF THE INVENTION

The object of the present invention, in a case previously described, is to achieve a fixture whereby artificial teeth or a tooth bridge construction can be successfully retained in an upper jaw with such properties that it does not fulfil the dimensioned or retention force demands normally required for such a procedure. Additionally, the invention may be utilized for obtaining a fixture to optimize positioned and retentioned fixation by the reconstruction of joints, e.g. finger and wrist-joints.

This is achieved by the use of the previously described anchoring element having substantially cylindrical shape and contralateral ends of different diameters, wherein the end portion with the smaller diameter is intended to be inserted into the zygomatic bone and is at least partially threaded whereas the other end part with the larger diameter with its at least partly threaded portion is intended to be retained in the maxillar bone and both threaded parts having the same pitch.

Both threaded parts may suitably converge with each other to form a continuous outer thread with different diameters.

According to a suitable embodiment of the invention the anchoring element can have a nonthreaded middle zone between the threaded portions of the end parts.

According to a further embodiment of the invention by its use as the mentioned anchoring element for fixation of artificial teeth or bridge constructions, the anchoring element is designed to be retained by its tooth-adjacent part in the maxilla and its distal part (insertion part) in the zygomatic, whereby the stress forces in the maxilla are relieved.

In order to achieve this the length of the anchoring element is suitably dimensioned for retention in the maxilla with its tooth-adjacent part and in the zygomatic with its insertion part and is supplied with means of retention of prosthetic elements at its tooth-adjacent end.

It is preferred for the diameter of the fixture to be larger over a substantial extension from its proximal end than over a substantial extension from its distal end, the outer diameter of the external threads in both portions being different but the distal and proximal external threads having the same pitch.

It is preferred for the fixation means to comprise a bore with internal threads and at least one abutment area for the tooth prosthesis or bridge, and for the bore to be positioned at an angle in respect of the central axis.

It is furthermore preferred that the angle comprised between the central axis of the fixture and the bore axis of the fixation means is between 15° and 60°, preferably about 45° or alternatively with a possibility for adjustment of this angle within a suitable range.

At its distal end the fixture according to the invention can be provided with a bore and through slits extending from the portion near the distal end or from that end in direction of the proximal end. It is also appropriate for the distal end to be somewhat bevelled. The threads can have self-tapping design.

According to another preferred aspect of the invention a non-treaded intermediate portion is arranged between the proximal and the distal external threads. It is preferred for the intermediate portion to have the same outer diameter as the outer diameter of the distal threads. This intermediate portion preferably is somewhat smaller than the distance between the sides of the zygomatic bone and the upper jaw facing each other.

According to a further embodiment a periosteal plate is placed around the gingival penetration area at the tooth-adjacent end of the anchoring element, whereby this plate is porous and is having a thickness of between 0,1–0,3 mm and suitably is supplied with a concentric hole with a diameter slightly larger than the greatest outer diameter of the anchoring element.

The present invention is also disclosing a method for attaching said fixture to the jaw bone and the zygomatic bone, said method comprising:
 (a) making a hole in the jaw bone,
 (b) making a hole in the zygomatic bone in line with the hole in the jaw bone, the hole in the zygomatic bone being given a smaller diameter than the hole in the jaw bone, insertion of a fixture with first external threads adapted to the diameter of the hole in the zygomatic bone, said first external threads having substantial extension from the one end of the fixture, and second external threads adapted to the diameter of the hole in the jaw bone, said second external threads having substantial extension between the second end of the fixture and the first external threads, said fixture end bordering the first outer threads being inserted first, (d) simultaneous screwing-on of the fixture into both holes, (e) orienting the screwed-on fixture by rotating it around its longitudinal axis, thereby positioning a bore at the free end of the fixture provided with inner threads in a tilting position in respect of the longitudinal axis of the fixture such as to allow anatomically correct mounting of the dental prosthesis or bridge, (f) mounting the dental prosthesis or the bridge on the fixture.

It is preferred for the screwing-on of the fixture to comprise self-tapping action.

The above objects, features and advantages of the invention will become apparent from the following description and appended claims, taken in conjunction with the accompanying drawings, without being limited to the shown embodiments.

DESCRIPTION OF PREFERRED EMBODIMENTS

In principle the anchoring element shown in the figures is mainly cylindrical and at one end, the so called supporting end, supplied with supporting means to receive directly or indirectly after heeling into the bone, prostheses, artificial join components, tooth bridges, artificial teeth etc. Such anchoring elements are previously described, cp. U.S. Pat. No. 5,064,425, showing the so called insertion end supplied with an outer thread, whereby the anchoring element is screwed into a prefabricated drilled hole with a slightly smaller diameter than the outer diameter of the thread on the anchoring element.

In this case the thread should preferably be self-tapping, as exemplified in U.S. Pat. No. 5,064,425.

In order to achieve optimal heeling and osseointegration with surrounding tissue, the surface of the anchoring element should preferably be formed with micropits within the size range of 10–1000 nm, as e.g. described in U.S. Pat. No. 4,330,891.

In the enclosed drawings, one of many possible indications for a suggested anchoring element according to the invention is illustrated, namely for the retention of artificial teeth or bridge constructions in partients with different defects in the jawbone.

By the use of the suggested anchoring element the possibility exists of a double anchoring in the maxilla and the zygomatic bone.

The invention may naturally also be utilized for many other applications, e.g. long bones may be used for such a double anchoring principle. The anchoring element shown in FIG. 1 is prepared in one piece of pure titanium and mainly built up of two adjacent and lined up cylinder-shaped segments.

Figure 1:
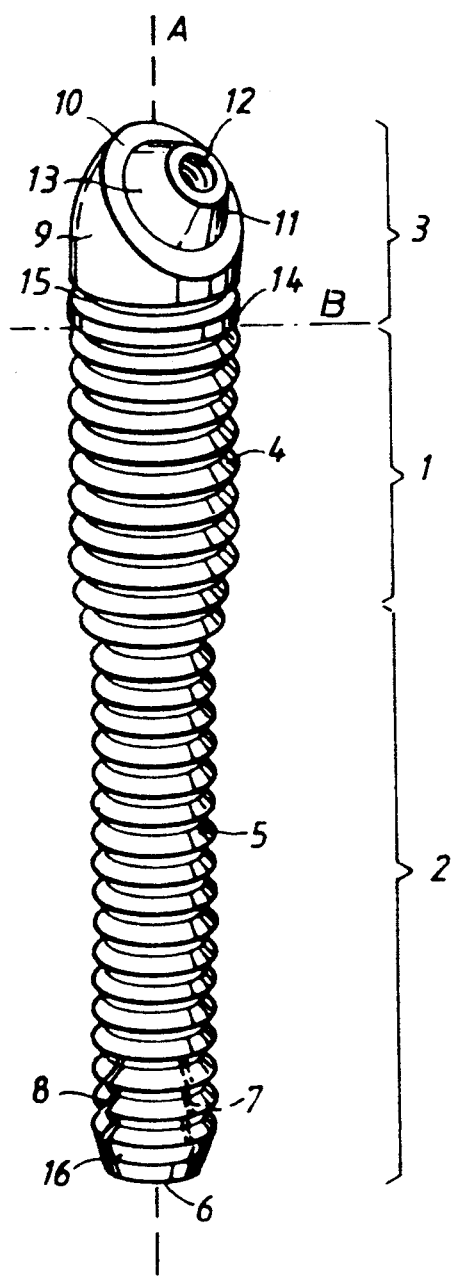
FIG. 1 shows an anchoring element according to a first embodiment of the invention in a somewhat lateral side view.

The fixture shown in FIG. 1 is manufactured as a single piece of pure titanium and essentially composed of two cylindric segments 1, 2 bordering each other and in being in alignment, wherein the segment proximal to the jaw and having a diameter larger than that of the segment distal to the jaw 2 is designated by 1.

The outside of the fixture is threaded, except for a mounting portion extending from the proximal end of the fixture and connected to the cylindric proximal segment 1. The outer threads comprise first threads 4 on the proximal cylindric segment 1 and second threads 5 on the distal cylindric segment 2. The pitch is the same for both threads 4, 5 merging at the border zone between the cylindric segments. The inner diameter of first threads 4 is somewhat but not much larger than the outer diameter of the second threads 5. Threads 4, 5 are self-tapping.

A symmetrically centred bore (not shown) extends from the distal end 6 and has an extension corresponding to about half the length of the distal segment 2. Two through slits 7, 8 arranged symmetrically in segment 2 and in its longitudinal direction extend from a plane perpendicular to the central axis near the distal end 6 by a length of about three thread pitches. Slits 7, 8 establish communication between the outside of distal segment 2 and the symmetrically centred bore arranged therein for transport of bone material removed by ablation. The outside of distal segment 2 is bevelled (bevelling 16) towards distal end 6.

The mounting section 3 is contained within a cylindric chamber with a diameter corresponding to the outer diameter of cylindric segment 1. The mounting segment 3 comprises a base portion 9 having the form of a cylindric body dissected by a plane at an angle of 45° i respect of the cylinder axis. The circular basis of base portion 9 is connected to the proximal end of proximal cylindric segment 1 with which it merges. Nearest to the proximal cylindric segment 1 base portion 9 has an annular flange 14 to which an annular groove 15 connects in direction of the proximal end. End face 10 of base portion 9 is defined by the aforementioned dissecting plane and, at its proximal zone, smoothly rounded joins the cylinder mantle of base section 9, the beading decreasing gradually towards the distal portion of the base section. Because of the bevelling the profile of end face 10 is substantially circular. In its center end face 10 has a bore 12 running at an angle of 45° in respect of longitudinal axis A for cylinder segments 1 and 2, i.e., for the fixture. At bore 12 base section 9 is extended under formation of a frustrum of a cone 11 tapering in direction away from base section 9. Mantle surface 13 of the cone frustrum 11 and the annular end face 10 are designed for sealing abutment of a dental prosthesis or bridge (not shown) that can be mounted on the base portion by screw means.

The parts of the fixture according to the invention in contact with living bone tissue have a surface promoting integration, preferably a surface covered by micropits or similar surface irregularities in the order of 10–1,000 nm.

Figure 2:
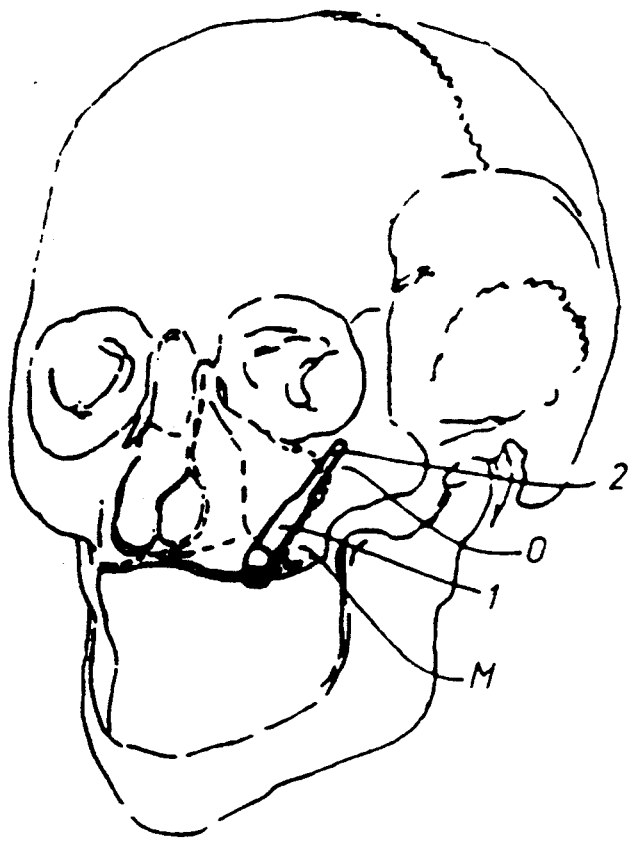
FIG. 2 shows a schematic view of the orientation of the anchoring element in relation to the maxilla and the zygomatic bone, in situ after operation.

Implantation starts by providing in the maxilla a bore with a diameter corresponding to the inner diameter of threads 4 and at an angle deviating about 45° from the vertical (the longitudinal axis of the human body in an upright position), followed by a bore in the zygomatic bone having a diameter corresponding to the inner diameter of threads 5 and in line with the first hole. Thereupon the fixture is inserted with its narrow end 6 into the hole in the upper jaw until, by means of its bevelled portion, it comes into engagement with the hole arranged in the zygomatic bone. Thereupon the fixture is screwed on into the hole in the zygomatic bone in a self-taping manner and, after threads 4 having reached the jaw bone, also simultaneously into the latter in a self-taping manner. When attaining a sufficient insertion depth for the fixture, such depth being defined by the fixture's free end having the correct distance from the jaw bone, the screwing process is stopped. By fine tuning, that is, anti-clockwise or clockwise rotation around its longitudinal axis, bore 12 provided with internal threads is brought into correct position for mounting of the prosthesis, i.e., in a position in which bore 12 is substantially parallel with the longitudinal axis of the human body. The position for an implanted fixture according to the invention is schematically shown in FIG. 2; the zygomatic bone has been designated by O and the maxilla by M.

The dental prosthesis or bridge can be mounted after surgery or after a healing period during which the fixture is progressively anchored in bone tissue.

The length of the fixture and cylindric sections 1 and 2 and the angle of bore 12 in base portion 9 are adapted to the anatomical requirements of the individual patient. A limited range of fixtures according to the invention, including fixtures of varied total length, varied ratio of length of the cylindric sections and varied angle of bore 12 in base section 9 in relation to the longitudinal axis of the fixture, will suffice for covering the needs of most patients.

It is also possible to produce the fixture in two parts, a separate base part 9 and a part 1, 2 provided with external threads. The base part and the part with external threads can be connected in various ways, for instance, by a symmetrically centred tap positioned on the end of base part 9 facing away from bore 12, said tap being arranged for screwing on into a threaded bore in the free end of part 1 provided with external threads, both parts otherwise having planar abutting surfaces (line B in FIG. 1 indicates their position) for abutment against each other.

Figure 3:
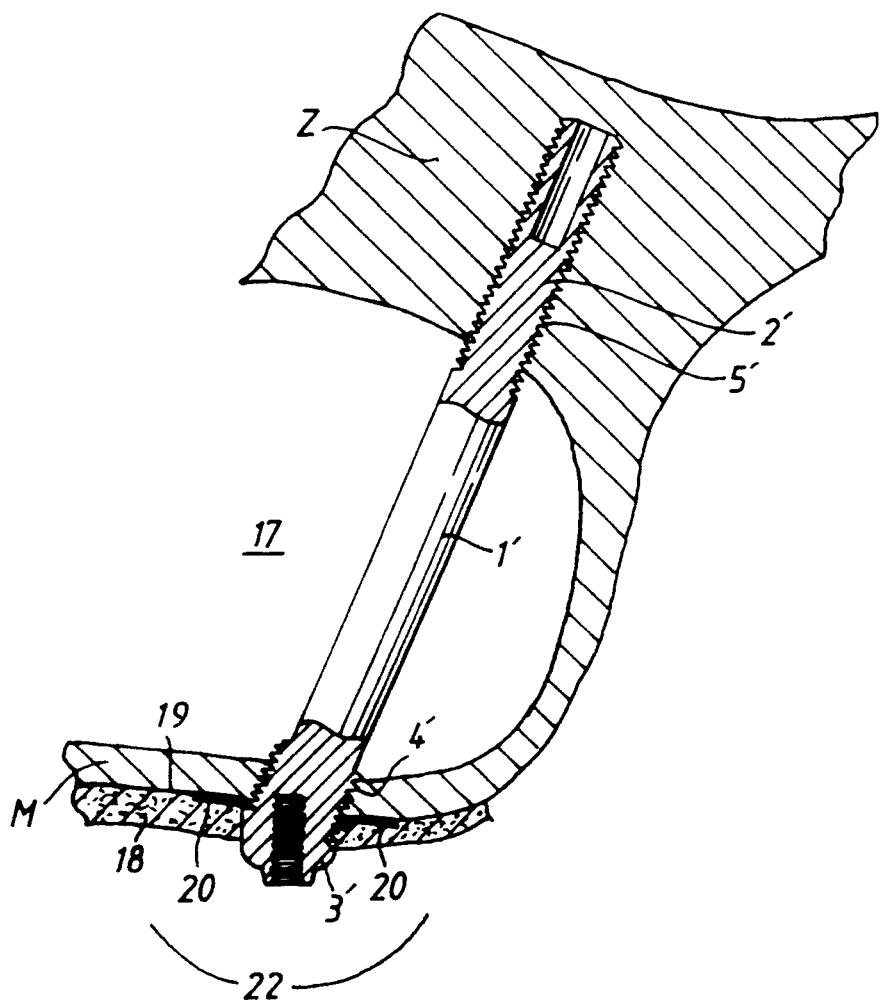
FIG. 3 shows an alternative embodiment of the anchoring element in situ after operation and supplied with a periosteal plate, and FIG. 4 a view of the plate shown in FIG. 3.

In a second embodiment of the fixture according to the invention shown in FIG. 3 only the proximal portion of the proximal segment 1' has first external threads 4'. The rest of the proximal segment 1' has a polished surface, i.e., essentially the portion positioned upon implantation in the maxillary sinus 17 between the maxilla M and the zygomatic bone Z. First external threads 4' thus have an extension essentially corresponding to the depth of the through bore provided in the maxilla M in preparation for implantation. The distal sediment 2' is provided with corresponding second external threads 5'.

Figure 4:
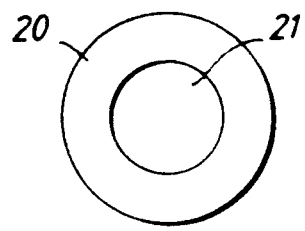

As is also shown in FIG. 3 this second embodiment can be provided (as can the first embodiment shown in FIG. 1) with a periosteal plate or foil 20 for enhancement of integration of the implant with living tissue in an area where the distal end zone of distal portion 2' with mounting portion 3' emerges from the through bore in the maxilla M. The periosteal plate or foil 20 is a porous disc of thin pure titanium, preferably from about 0.1 to about 0.3 mm thick and having a concentric hole 21 with a diameter slightly larger than the largest outer diameter of the fixture 1', 2', 3', allowing plate or foil 20 to be fitted like a collar around the part of the fixture protruding from the maxilla M. Periosteal plate or foil 20 is fitted with its one side against outer surface 19 of the maxilla M after partial removal of the periosteum 18 (thickness of periosteum 18 is exaggerated in FIG. 3 for reasons of comprehensiveness) which is then folded back against the other side of the periosteal plate or foil 20. The pores (not shown in FIG. 3 and 4) in the periosteal foil or plate 20 are through pores and provide for communication between both sides of foil or plate 20; it is preferred for the pores to have an average diameter of from about 0.1 to about 0.01 mm. The periosteal foil or plate 20 promotes anchoring of the fixture around its proximal part and reduces the risk of communication between the oral cavity 22 and the maxillary sinus 17.

I claim:

1. A method for attaching a fixture for holding a dental prosthesis or bridge to a jaw bone and a zygomatic bone, said method including steps of:
   (a) making a first hole of a first diameter in the jaw bone,
   (b) making a second hole of a second diameter in the zygomatic bone in axial alignment with the first hole, with the second diameter being smaller than the first diameter,
   (c) inserting a fixture having first and second external threads adapted to the respective first and second diameters, said first external threads being relatively close to one end of the fixture and said second external threads being remote from said one end and said fixture having its other end disposed at a substantial distance from the first external threads,
   (d) during inserting of said fixture said other end being moved axially through said first hole and then entering said second hole,
   (e) simultaneous screwing-on of the fixture with the first and second external threads being in the respective first and second holes,
   (f) orienting the fixture while same is being screwed-on by rotating the fixture around its longitudinal axis, thereby operatively positioning a bore that is in the fixture at said one end thereof, said bore having internal threads for mounting a dental prosthesis or a bridge on the fixture, with internal threads being in a tilt position with respect to the longitudinal axis of the fixture such as to permit anatomically correct positioning of a dental prosthesis or bridge that is mounted on said fixture, and
   (g) mounting the dental prosthesis or the bridge on the fixture by threadably engaging said internal threads with external threads on the dental prosthesis or the bridge.

2. The method of claim 1, characterized in that the screwing-on of the fixture comprises self-tapping action by both the first and second external threads.

3. The method of claim 1 also includes steps of:
   (h) preparing a free jaw bone surface around the first hole, and
   (i) fitting a thin plate collar of biocompatible material, preferably of titanium and provided with through pores, around said hole, with one side of said collar abutting said freed jaw bone surface.

4. The method of claim 3, characterized in that the screwing-on of the fixture comprises self-tapping action by both the first and second external threads.

* * * * *